US012751981B2

(12) United States Patent
Naude et al.

(10) Patent No.: US 12,751,981 B2
(45) Date of Patent: Oct. 6, 2026

(54) COMPOSITION FOR IMPROVING THE MICROBIOME

(71) Applicant: IIAA Limited, Borehamwood (GB)

(72) Inventors: Paul Naude, Bristol (GB); Lorraine Perretta, London (GB); Tanya Meyer, St. Albans (GB)

(73) Assignee: IIAA Limited, Borehamwood (GB)

( * ) Notice: Subject to any disclaimer, the term of this patent is extended or adjusted under 35 U.S.C. 154(b) by 609 days.

(21) Appl. No.: 18/111,246

(22) Filed: Feb. 17, 2023

(65) Prior Publication Data

US 2023/0277438 A1 Sep. 7, 2023

Related U.S. Application Data

(63) Continuation of application No. PCT/GB2021/052174, filed on Aug. 20, 2021.

(30) Foreign Application Priority Data

Aug. 21, 2020 (GB) ...................................... 2013110

(51) Int. Cl.

| | |
|---|---|
| ***A61K 35/747*** | (2015.01) |
| ***A61K 8/9728*** | (2017.01) |
| ***A61K 8/99*** | (2017.01) |
| ***A61K 36/064*** | (2006.01) |
| ***A61P 17/00*** | (2006.01) |
| ***A61P 17/10*** | (2006.01) |
| ***A61Q 19/00*** | (2006.01) |

(52) U.S. Cl.

CPC .......... *A61K 35/747* (2013.01); *A61K 8/9728* (2017.08); *A61K 8/99* (2013.01); *A61K 36/064* (2013.01); *A61P 17/00* (2018.01); *A61P 17/10* (2018.01); *A61Q 19/00* (2013.01); *A61Q 19/008* (2013.01); *A61K 2800/92* (2013.01)

(58) Field of Classification Search

None

See application file for complete search history.

(56) References Cited

U.S. PATENT DOCUMENTS

| | | | |
|---|---|---|---|
| 6,841,149 | B1 | 1/2005 | Spangler et al. |
| 2010/0226892 | A1 | 9/2010 | Gueniche |

FOREIGN PATENT DOCUMENTS

| | | | |
|---|---|---|---|
| WO | 2019111189 A1 | 6/2019 | |

OTHER PUBLICATIONS

Paetzold et al., "Skin microbiome modulation induced by probiotic solutions", Microbiome, vol. 7(95), pp. 1-9. (Year: 2019).*

Pidcock et al., "Application of nontraditional meat starter cultures in production of Hungarian salami", International Journal of Food Microbiology, vol. 76, pp. 75-81. (Year: 2002).*

Rahmayani et al., "The Effect of Oral Probiotic on the Interleukin-10 Serum Levels of Acne Vulgaris", Open Access Macedonian Journal of Medical Science, vol. 7(19), pp. 3249-3252. (Year: 2019).*

Villot et al., "Early supplementation of *Saccharomyces cerevisiae boulardii* CNCM I-1079 in newborn dairy calves increases IgA production in the intestine at 1 week of age", Journal of Dairy Science, vol. 103, pp. 8615-8628; electronically published Jul. 16, 2020. (Year: 2020).*

Aknetherapie mit *Saccharomyces boulardii*; Akt. Dermatol. 17 (1991) 206-209 Georg Thieme Verlag Stuttgart; New York.

Current and Future Applications of Probiotics; Current Nutrition & Food Science, 2011, Collado MC et al., 7, 170-180, retrieved on May 25, 2021.

Immune enhancing effects of Lactobacillus acidophilus Lafti L10 and Lactobacillus paracasei Lafti L 26 in mice; Paturi, Int'l Journal of Food Microbiology 115, 2007; 115-118.

Mintel Probiotic of (*Saccharomyces boulardii* and all child ingredients; Retrieved from the Internet: URL:http://www.gnpd.com The whole document.

Mintel: "Mintel_Search_for_Products_Bluebonnet_Single_Daily_Probiotic"Retrieved from the Internet: URL:http://www.gnpd.com The whole document.

Mintel: "Mintel_Search_for_Products_Imubio"Retrieved from the Internet: URL:http://www.gnpd.com The whole document.

Mintel: "Mintel_Search_for_Products_Primal_Defense"Retrieved from the Internet: URL:http://www.gnpd.com The whole document.

Mintel: "Mintel_Search_for_Products_Probactiol_duo"Retrieved from the Internet: URL:http://www.gnpd.com The whole document.

Mintel: "Mintel_Search_for_Products_The_Real_Thing_Probiotic"Retrieved from the Internet: URL:http://www.gnpd.com The whole document.

Mintel: "Mintel_Search_for_Products_Travelers_Defense_and_Immunity"Retrieved from the Internet: URL:http://www.gnpd.com The whole document.

Probiotics; Kligler, Benjamin and Cohrssen, Andreas; American Family Physician, 2008; 78_9_1073-1078; URL:www.aafp.org/afp.

Intellectual Property Office Search Report from Application GB2013110.8 dated Jun. 9, 2021.

The International Search Report for PCT application PCT/GB2021/052174 filed on Aug. 20, 2021 dated Nov. 8, 2021.

* cited by examiner

*Primary Examiner* — Grant C Currens

(74) *Attorney, Agent, or Firm* — Veros Legal Solutions, LLP

(57) ABSTRACT

A composition comprising *Lactobacillus paracasei* and *Saccharomyces boulardii* is disclosed. The composition for use as a medicament, the composition for use in the treatment of a skin disease, a method of improving the appearance of the skin of a subject comprising orally administering the composition to the subject and a method of altering the microbiome of the skin of a subject comprising orally administering the composition to the subject are also disclosed.

11 Claims, 4 Drawing Sheets

COMPOSITION FOR IMPROVING THE MICROBIOME

CROSS-REFERENCE TO RELATED APPLICATIONS

This application is a Continuation of PCT Application No. PCT/GB2021/052174 filed Aug. 20, 2021, which claims the benefit of GB Application No. 2013110.8, filed Aug. 21, 2020, the entire contents of each are hereby incorporated by reference in their entirety herein.

FIELD OF THE INVENTION

The present invention concerns compositions, especially compositions for oral administration, for improving the microbiome. More particularly, but not exclusively, this invention concerns microbial compositions for altering the microbiome, in particular the skin microbiome. The invention also concerns related methods and uses.

BACKGROUND OF THE INVENTION

Humans have long sought to improve the appearance of their skin by cosmetic intervention. Undesirable skin imperfections and characteristics include dry skin, oily skin, wrinkles and fine lines, poor elasticity, peeling or flaky skin, roughness and redness. Of particular interest to consumers is the improvement in or reduction of such imperfections and characteristics, particularly when associated with the skin of the face.

Many factors contribute to problem skin, including sebum. Sebum is secreted by sebaceous glands and is primarily composed of triglycerides, wax esters, squalene and fatty acids. Excess sebum production causes an oily or greasy appearance of the skin, while conversely an underproduction of sebum can result in a dry and dull appearance of the skin. Bacterial imbalances, hormone fluctuation, stress, increased keratinisation and diet also have a role in the appearance of the skin.

Several microbiome species have been associated with problem skin, such as *Cutibacterium acnes* (formerly known as *Proprionibacterium acnes*). *Cutibacterium acnes* feeds on the fatty acids found in sebum. Sebum over-secretion, abnormal keratinocyte desquamation (the shedding of keratin containing skin cells) leading to ductal obstruction, and inflammation are also caused by *Cutibacterium acnes*. Although *Cutibacterium acnes* is found on healthy skin, an imbalance of *Cutibacterium acnes* can result in the skin condition acne vulgaris. Acne vulgaris is a chronic inflammatory disease that is associated with over-activity of the oil, or sebaceous, glands in the skin and the blockage of those glands and inflammation of the skin. It is characterised by comedones and pimples, particularly on the face, back and chest, and in severe cases cysts and nodules result in scarring. Acne vulgaris is prevalent, with approximately 85% of people aged between 12 and 25 affected to some extent.

Atopic dermatitis (eczema) is a chronic or recurrent inflammatory skin disease characterised by areas of severe itching, redness, scaling and loss of the surface skin. Atopic dermatitis affects 15-30% of children and 2-10% of adults (Salem et al. Frontiers in Microbiology, 2018, 9, Article 459). The diet-microbiome theory hypothesises that the increased prevalence of allergic diseases, such as atopic dermatitis, results at least in part from the less robust state of immune homeostasis rather than an overresponse to environmental triggers. The western diet is thought to impair the gut microbiome's contribution to immune homeostasis and there has been a disproportionate rise of allergic diseases in the western world.

A further skin disease that is linked to the microbiome is psoriasis. Psoriasis is an immune-mediated chronic inflammatory dermatosis which typically involves periods of no or mild symptoms followed by reoccurring flair ups where more severe symptoms occur. Psoriasis is thought to be caused by dysfunction of the immune system triggering the skin to regenerate at a faster rate than normal. The condition is characterised by red, flaky and crusty patches of skin covered in silvery scales which can occur anywhere on the body but are most common on the elbows, knees, scalp and trunk. This condition affects around 2% of people in the UK.

Rosacea is a long-term skin condition that mainly affects the face. Symptoms include redness and visible blood vessels across the nose, cheeks, forehead and chin and may also include dry skin, swelling, particularly around the eyes, pimples, yellow-orange patches on the skin, sore eyelids and thickened skin, particularly around the nose.

The human microbiome genome is the combined genetic material of the microorganisms found in and on the human body. Between 2007 and 2013, scientists mapped the microbiome genome to aid the understanding of the role the various microorganisms play and their impact on human health. The human microbiome genome consists of the genes of 10-100 trillion symbiotic microbial cells (Ursell et al. Nutr Rev. 2012; 70(Suppl): S38-S44).

The microbial genome can be assessed in different sites of the body. For example, the microbiome may be assessed in the gut (or region thereof) or on the skin (or region thereof). The adult intestine, particularly the lower gut, hosts a diverse range of bacterial, fungal and viral species and is particularly important for overall human health by protecting against diseases, breaking down food to release energy, and also producing essential vitamins. For example, the gut microbiome breaks down indigestible complex polysaccharides and also releases important nutritional components such as vitamin K. Metabolites such as retinoic acid, and polysaccharide A from *Bacteroides fragilis*, and microbes such as *Faecalibacterium prausnitzii* and bacteria belonging to the Clostridium cluster IV and XI, promote the accumulation of regulatory T cells which facilitate anti-inflammatory responses.

An imbalance in the microbiome, known as dysbiosis, can itself result in reduced health and disease. There are many factors which can contribute to dysbiosis including medications, stress and diet. For example, antibiotics may deplete the salubrious microbiome as well as pathogenic bacteria.

Although the mechanisms are not fully understood, a complex relationship exists between gut health and the health of the skin (Salem et al. Frontiers in Microbiology, 2018, 9, Article 459). There is some evidence that metathesis of intestinal microbes and their metabolites to the skin can occur, which alters the skins physiology, pathology, immune response and skin microbiome. The intestinal microbiome also contributes to skin allostasis, which is the restoration of homeostasis after a disturbance or stressor. Acne vulgaris, atopic dermatitis and psoriasis are three common diseases that are influenced by the gut microbiome (Salem et al. Frontiers in Microbiology, 2018, 9, Article 459).

The gut microbiome is greatly influence by diet and thus may be altered by the administration of probiotic supplements. Probiotic supplementation is the administration of live beneficial bacteria and yeasts to the gut. Due to the link between inflammatory diseases such as acne vulgaris and the microbiome of the gut, altering the microbiome of the gut may give beneficial therapeutic effects, such as prevention or management of various skin conditions. A combination of pro-and prebiotics also offer health benefits.

Probiotic supplements represent a promising option for improving the appearance of skin. However, the field of probiotic supplements, particularly for use in improving the appearance of skin, is in its infancy. There is therefore a need to expand the range of probiotic supplements to those that can improve the appearance of skin, such as by normalising levels of sebum, reducing redness or increasing the elasticity of the skin. Additionally, it would be advantageous to expand the use of probiotic supplements to the treatment of skin disorders such as acne vulgaris.

The present invention seeks to mitigate the above-mentioned problems. Alternatively or additionally, the present invention seeks to provide an improved method of improving the appearance of the skin by administering a composition comprising probiotics. Alternatively, or additionally, the present invention seeks to provide an improved method for altering the microbiome of the skin by orally administering a composition comprising a probiotic.

SUMMARY OF THE INVENTION

According to a first aspect of the invention there is provided a method of improving the appearance, for example the cosmetic appearance, of the skin of a subject, wherein the subject is a human being, the method comprising:

(i) orally administering to the subject a composition comprising *Lactobacillus paracasei* and *Saccharomyces boulardii* and, (ii) repeating step (i) until a cosmetically beneficial improvement in the appearance of the skin of the subject has occurred.

Such a bacterium and yeast may be used to improve the appearance of the skin, normalise the concentration of sebum on the skin, and may be used to improve the appearance of inflammatory skin diseases or even treat such diseases. A composition comprising *Lactobacillus paracasei* and *Saccharomyces boulardii* may be particularly useful in reducing the appearance of, or treating inflammatory skin diseases such as acne vulgaris, atopic dermatitis, psoriasis and rosacea.

Preferably, the *Lactobacillus paracasei* comprises the strain Lafti L26 AF. Preferably, the *Saccharomyces boulardii* comprises the strain *Saccharomyces cerevisiae boulardii* CNCM-I-1079. Preferably, the *Lactobacillus paracasei* comprises the strain Lafti L26 AF, and the *Saccharomyces boulardii* comprises the strain *Saccharomyces cerevisiae boulardii* CNCM-I-1079. These specific strains of *Lactobacillus paracasei* and *Saccharomyces boulardii* may be particularly advantageous for improving the appearance of the skin or treating an inflammatory skin disease over other strains of *Lactobacillus paracasei* and *Saccharomyces boulardii*.

Preferably, the composition at the point of manufacture comprises between about $1\times10^9$ and about $20\times10^9$ colony forming units (CFUs) of *Lactobacillus paracasei* and between about $1\times10^9$ and about $4\times10^9$ of *Saccharomyces boulardii*, preferably wherein the composition comprises about $12\times10^9$ or more colony forming units (CFUs) of *Lactobacillus paracasei* and about $2.5\times10^9$ CFU or more of *Saccharomyces boulardii*. Such a concentration of each of *Lactobacillus paracasei* and *Saccharomyces boulardii* may advantageously result in the improvement of the appearance of the skin or treatment of an inflammatory skin disease of the skin.

Preferably, the composition further comprises *Lactobacillus helveticus*, preferably wherein the *Lactobacillus helveticus* comprises the strain Lafti L10 ND. The presence of *Lactobacillus helveticus* in the composition may further improve the appearance of the skin of a subject that has orally been administered the composition or may treat inflammatory skin diseases. Preferably, the composition comprises at the point of manufacture between about $1\times10^9$ and about $8\times10^9$ colony forming units (CFUs) of *Lactobacillus helveticus*, preferably wherein the composition comprises about $4\times10^9$ or more colony forming units (CFUs) of *Lactobacillus helveticus*.

Preferably, the composition further comprises further comprising *Bifidobacterium bifidum*, preferably wherein the *Bifidobacterium bifidum* comprises the strain Rosell-71 (R0071). Preferably, the composition comprises at the point of manufacture between about $1\times10^9$ and about $8\times10^9$ colony forming units (CFUs) of *Bifidobacterium bifidum*, preferably wherein the composition comprises about $4\times10^9$ or more colony forming units (CFUs) of *Bifidobacterium bifidum*.

Preferably, the total amount of *Lactobacillus paracasei* and *Saccharomyces boulardii*, and optionally each of *Lactobacillus helveticus* and *Bifidobacterium bifidum* is at least $5\times10^9$ colony forming units at the point of oral administration of the composition. Due to the fact that bacteria will naturally die-off once the composition has been formulated, the composition contains at least at least $5\times10^9$ colony forming units of all yeast and bacteria strains at the point of oral administration. This may alternatively be measured as a concentration of at least at least $5\times10^9$ colony forming units of all yeast and bacteria strains at the best before date of the composition i.e. the date at which at any later date the composition is deemed no longer fit for human consumption.

Preferably, the composition further comprises a source of zinc, preferably wherein the source of zinc is zinc oxide. A source of zinc may improve the appearance of the skin, for example by having an anti-inflammatory effect and/or in reducing the production of sebum by the skin. Preferably, the composition comprises between about 0.1 mg and about 25 mg of a source of zinc, such as between about 1 mg and about 5 mg of a source of zinc, most preferably wherein the composition comprises about 2 mg of a source of zinc.

According to a second aspect of the invention, there is provided a method of altering the microbiome of the skin of a subject, wherein the subject is a human being, the method comprising:

(i) orally administering to the subject a composition comprising *Lactobacillus paracasei* and *Saccharomyces boulardii*, and, (ii) repeating step (i) until the microbiome of the skin of a subject has altered.

The composition may optionally be as described in reference to other aspects of the invention, especially in reference to the first aspect of the invention.

According to a third aspect of the invention there is provided a composition comprising *Lactobacillus paracasei* and *Saccharomyces boulardii*, wherein the *Lactobacillus paracasei* comprises the strain Lafti L26 AF. The composition may optionally be as described in reference to other aspects of the invention, especially in reference to the first aspect of the invention.

According to a fourth aspect of the invention, there is provided a capsule for oral administration comprising the composition of the third aspect of the invention. The composition may optionally be as described in reference to other aspects of the invention, especially in reference to the first aspect of the invention. The capsule may optionally further comprise a biologically compatible filler.

According to a fifth aspect of the invention there is provided a liquid for oral administration comprising the composition of the third aspect of the invention. The liquid could, for example, be in the form of a drink. The composition may optionally be as described in reference to other aspects of the invention, especially in reference to the first aspect of the invention.

According to a sixth aspect of the invention, is a composition according to the third aspect of the invention for use as a medicament. The invention also provides a composition comprising *Lactobacillus paracasei* and *Saccharomyces boulardii* for use in the treatment of a skin disease. More preferably, wherein the skin disease is an inflammatory skin disease such as one or more of acne vulgaris, atopic dermatitis, psoriasis and rosacea. The composition may optionally be as described in reference to other aspects of the invention, especially in reference to the first aspect of the invention.

A composition relating to all aspects of the invention may preferably be in the form of a tablet, powder, capsule, drink or food for oral administration. Such forms of the composition will be easy to administer to a subject or by the subject and can be consumed in both a clinical or non-clinical setting.

Methods of the invention according to its first aspect are practiced on a human subject. Preferably, said methods involve the administration of the composition, for example orally administered, in the form of a capsule, food or drink. Such forms of the composition can be taken easily orally by the subject.

Preferably, administration of the composition may be repeated once a day until a cosmetically beneficial improvement in the appearance of the skin of the subject has occurred.

Methods of the invention according to its second aspect may further comprise the step of:

(iii) further repeating step (i) in order to maintain the cosmetically beneficial improvement in the appearance of the skin of the subject, for example step (i) is repeated once a day for several months, for example three months.

It will be understood that step (i) may be repeated for as long as necessary for there to be observed an improvement in the appearance of the skin of a subject. Step (i) may also be repeated as long as necessary to maintain the improvement in the skin. Furthermore, step (i) may be repeated after a pause in administration of the composition, for example if the subject forgets to take the composition for several days, or if a significant improvement in the appearance of the skin is maintained for several months. Step (i) may be repeated if after pausing the administration of the composition, the subject experiences a decline in the appearance of the skin. In such a scenario, repeating step (i) may lead to a return of the skin to the improved condition or appearance.

Preferably, the cosmetically beneficial improvement of the skin is one or more improvement selected from the list of: increased elasticity, increased hydration, change of sebum secretion levels, reduced roughness, reduced redness, increased smoothness, reducing transepidermal water loss, reduction in the appearance of wrinkles and fine lines. In the case of a change in sebum secretion levels, this may be an increase in secretion following administering a composition according to the invention to the subject, if the subject usually experiences low levels of sebum secretion and hence dry skin. Conversely, the change in sebum secretion levels may be a decrease in sebum secretion following administering a composition according to the invention to the subject, if the subject usually experiences high levels of sebum secretion and oily or greasy skin. Most preferably, the cosmetically beneficial improvement of the skin is a reduction in sebum secretion.

Methods of the second aspect of the invention are methods of altering the skin microbiome.

Alteration of the skin biome can lead to an improvement in the appearance of the skin of a subject due to the complex relationship between the microbiome of the skin and diseases and conditions that affect the skin. Preferably, the alteration of the skin microbiome is characterised by a decrease in the bacteria *Cutibacterium* acnes. Thus, alteration in the skin biome may result in a reduction in the symptoms associated with acnes vulgaris, caused by an excess of *Cutibacterium* acnes, or may even treat acnes vulgaris in a subject.

Preferably, the method according to the second aspect of the invention, further comprises the step of:

(iii) further repeating step (i) in order to maintain the altered microbiome of the skin, for example step (i) is repeated once a day for several months, for example three months.

It will be understood that step (i) may be repeated for as long as necessary for the microbiome of the skin of a subject to change. Step (i) may also be repeated as long as necessary to maintain the change in the microbiome of the skin. Furthermore, step (i) may be repeated after a pause in administration of the composition, for example if the subject forgets to take the composition for several days, or if a significant change of the microbiome of the skin is maintained for several months. Step (i) may be repeated if after pausing the administration of the composition, the subject experiences a decline in the microbiome of the skin, for example an undesirable change in the microbiome of the skin such as an increase in the concentration of *Cutibacterium* acnes. In such a scenario, repeating step (i) may lead to a return of the skin to the improved skin microbiome, for example a microbiome with a lower concentration of acnes.

Preferably, the skin according to any aspect or embodiment of the invention is the skin of the face, neck or back of the subject, preferably wherein the skin is the skin of the face of the subject.

Preferably, the subject according to any aspect or embodiment of the invention is over the age of 16 years. Preferably, the subject according to any aspect or embodiment of the invention is female, between the age of 18 and 30 and diagnosed with acne vulgaris. Females in the age range of 18 to 30 are particularly prone to the skin condition acne vulgaris. The subject according to any aspect or embodiment of the invention may have a skin disorder, especially an immune mediated chronic inflammatory skin disorder. They may have one or more of acne vulgaris, atopic dermatitis, psoriasis and rosacea.

It will of course be appreciated that features described in relation to one aspect of the present invention may be incorporated into other aspects of the present invention. For example, the method of the invention may incorporate any of the features described with reference to the compositions of the invention and vice versa.

BRIEF DESCRIPTION OF THE DRAWINGS

Embodiments of the present invention will now be described by way of example only with reference to the accompanying schematic drawings of which.

DETAILED DESCRIPTION

Compositions

Figure 1:
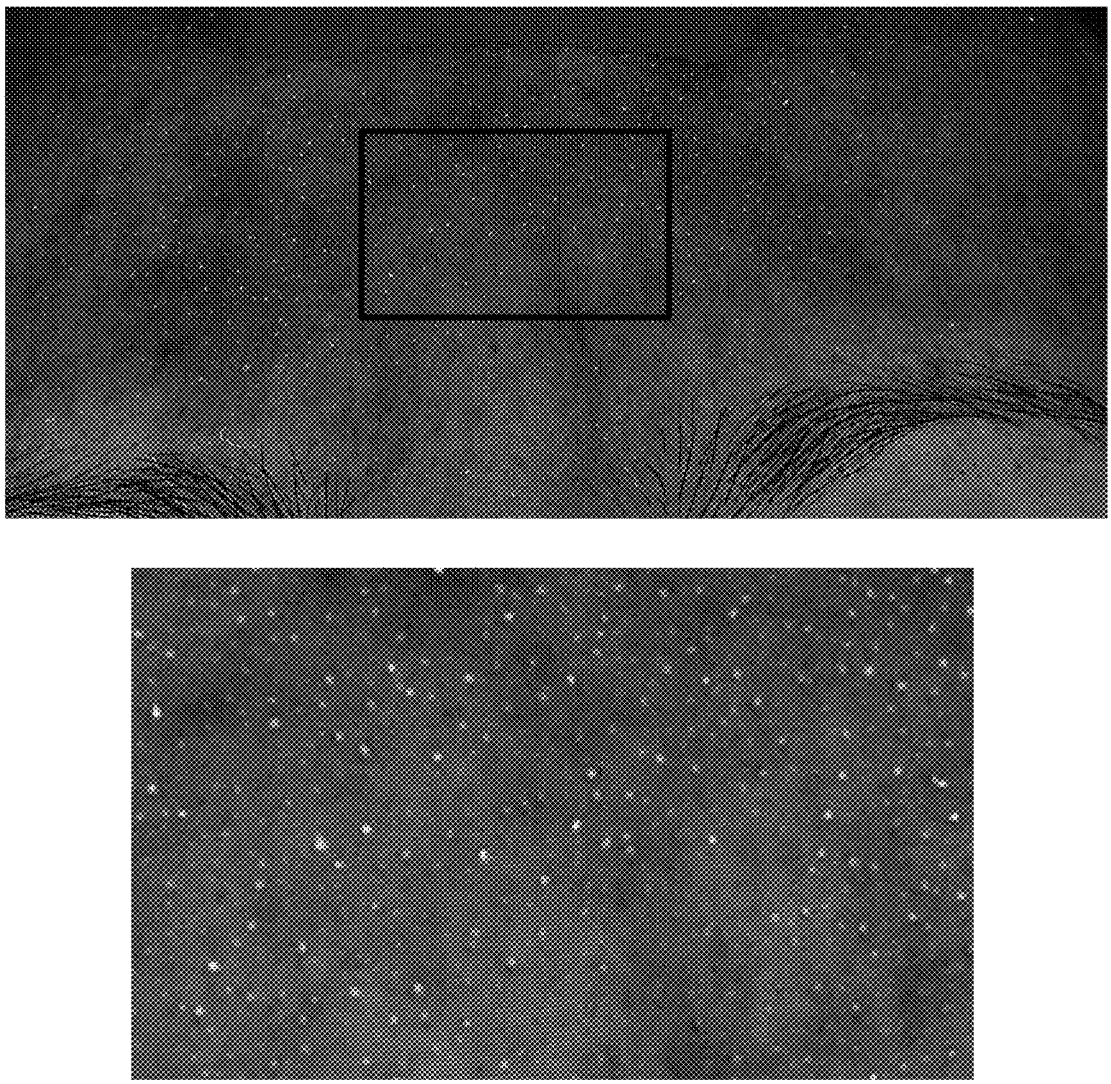
FIG. 1 shows an image taken of the forehead of subject 2 with UV (near 400 nm) facial imaging equipment before composition A was administered. The lower image is an expanded image of the section of the forehead highlighted in a box in the upper image. The white regions on the skin (corresponding to orange regions in the colour image) are caused by porphyrins which fluoresce under UV light.

Compositions according to the invention comprise *Lactobacillus paracasei* and *Saccharomyces boulardii*. These microbes are preferably provided in a substantially viable form. According to the third, fourth and fifth aspects of the invention, the *Lactobacillus paracasei* comprises the strain Lafti L26 AF. This feature is optional in other aspects of the invention but may be preferred according to certain embodiments of those aspects.

In certain embodiments the compositions may additionally comprise one or more further microbial organism. For example, the compositions may additionally comprise *Lactobacillus helveticus*. In certain embodiments the compositions may additionally comprise *Bifidobacterium bifidum*.

In certain embodiments the compositions may additionally comprise *Lactobacillus helveticus* and *Bifidobacterium bifidum*.

In certain embodiments the compositions may additionally comprise *Lactobacillus helveticus, Bifidobacterium bifidum* and zinc.

The taxonomy change for *Lactobacillus* was officially published in the International Journal of Systematic and Evolutionary Microbiology in April 2020 (Zheng, J. et al. (2020). A taxonomic note on the genus *Lactobacillus*: Description of 23 novel genera, emended description of the genus *Lactobacillus* Beijerinck 1901, and union of *Lactobacilluseae* and *Leuconostocaceae*. International Journal of Systematic and Evolutionary Microbiology, 70:2782-2858.) Consequently, new genera have been created in addition to the current *Lactobacillus*. It is to be noted that the species and the strains remain the same, the change only pertains to the genus.

| Previous taxonomy | Updated taxonomy |
|---|---|
| *Lactobacillus acidophilus* | *Lactobacillus acidophilus* |
| *Lactobacillus delbrueckii* subsp *bulgaricus* | *Lactobacillus delbrueckii* subsp *bulgaricus* |
| *Lactobacillus gasseri* | *Lactobacillus gasseri* |
| *Lactobacillus helveticus* | *Lactobacillus helveticus* |
| *Lactobacillus brevis* | *Levilactobacillus brevis* |
| *Lactobacillus casei* | *Lacticaseibacillus casei* |
| *Lactobacillus fermentum* | *Limosilactobacillus fermentum* |
| *Lactobacillus paracasei* | *Lacticaseibacillus paracasei* |
| *Lactobacillus plantarum* | *Lactiplantibacillus plantarum* |
| *Lactobacillus reuteri* | *Limosilactobacillus reuteri* |
| *Lactobacillus rhamnosus* | *Lacticaseibacillus rhamnosus* |
| *Lactobacillus salivarius* | *Ligilactobacillus salivarius* |

The previous taxonomy and updated taxonomy may be used interchangeably, for example herein.

Microbial Strains

Compositions according to the invention may in certain embodiments comprise one or more preferred strains as shown in the table below.

| Microbial species | Preferred strain |
|---|---|
| *Lactobacillus paracasei* | Lafti L26 AF |
| *Saccharomyces boulardii* | *Saccharomyces cerevisiae boulardii* CNCM -I-1079 |
| *Lactobacillus helveticus* | Lafti L10 ND |
| *Bifidobacterium bifidum* | Rosell-71 (R0071) |

According to certain embodiments, one or more of the microbial species may in an optional embodiment comprise an equivalent, corresponding, similar or derivative of the strain listed above. For example, it may comprise a redeposit of one of the strains listed above. It may be a strain which is isolated from the same or similar source as one of the strains listed above, or it may be a strain for which one of the strains listed above is an ancestral strain, that is to say it may be a strain which was been obtained by natural or artificial means from one of the specified strains.

Preferably, *Lactobacillus paracasei* as used in the invention will comprise a strain which is able to produce L(+) lactic acid and acetic acid. It preferably has a carbohydrate fermentation pattern allowing growth on API 50 CH medium. The Lafti L26 AF strain meets these criteria.

Preferably, the strain of microbial species is one which has been approved for human consumption. The strain may, for example, be on the EFSA QPS (qualified presumption of safety) list. It may be that the strain, or strains enhance immunity and/or reduce inflammation. It may be that the strain, or strains reduce inflammation of the skin. It may be that the strain, or strains improve the appearance of the skin, particularly the skin of the face.

In preferred embodiments, one or more strains of *Lactobacillus paracasei* are selected from the following table.

| Species | Strain |
|---|---|
| *Lactobacillus paracasei* | Lafti L26 AF |
| *Lactobacillus paracasei* | Med 14 |
| *Lactobacillus paracasei* | Nx-5850 |
| *Lactobacillus paracasei* | SD-5218 |

| Species | Strain |
|---|---|
| *Lactobacillus paracasei* | 8700:2 |
| *Lactobacillus paracasei* | ATC 5275 |
| *Lactobacillus paracasei* | CUL-08 |
| *Lactobacillus paracasei* | DSM 13434 |
| *Lactobacillus paracasei* | DSM 24733 |
| *Lactobacillus paracasei* | F-19 |
| *Lactobacillus paracasei* | GPS 4337 |
| *Lactobacillus paracasei* | GPS 4396 |
| *Lactobacillus paracasei* | HA-196 |
| *Lactobacillus paracasei* | HA-274 |
| *Lactobacillus paracasei* | IMC 502 |
| *Lactobacillus paracasei* | LP-33 |
| *Lactobacillus paracasei* | LPC12 |
| *Lactobacillus paracasei* | Lpc-00 |
| *Lactobacillus paracasei* | Lpc-37 |
| *Lactobacillus paracasei* | MED 24 |
| *Lactobacillus paracasei* | SD5275 |
| *Lactobacillus paracasei* | Shirota |
| *Lactobacillus paracasei* | UApc-04 |
| *Lactobacillus paracasei* | W20 |
| *Lactobacillus paracasei* | W72 |
| *Lactobacillus paracasei* | NCC 2461 |
| *Lactobacillus paracasei* | CBA L74 |

*Lactobacillus paracasei* is of the genus *Lacticaseibacillus*. In preferred embodiments, the composition of the invention may comprise further species of the genus *Lacticaseibacillus*. For example, the composition may further comprise *Lactobacillus casei* and/or *Lactobacillus rhamnosus*. Alternatively, the composition of the invention may comprise one or more species within the genus *Lacticasaeibacillus* instead of or alternatively to *Lactobacillus paracasei*. For example the composition of the invention may be absent *Lactobacillus paracasei* and instead comprise *Lactobacillus casei* and/or *Lactobacillus rhamnosus. Lactobacillus paracasei, Lactobacillus casei* and *Lactobacillus rhamnosus* are lactic acid producing species which have a similar function and therefore may in certain embodiments be used interchangeably.

It is preferred that all bacterial strains to be used in accordance with the invention have no transferrable antibiotic resistance genes.

In preferred embodiments, one or more strains of *Saccharomyces boulardii* are selected from the following table.

| Species | Strain |
|---|---|
| *Saccharomyces boulardii* | CNCM-I 1079 |
| *Saccharomyces boulardii* | CNCM I-745 |
| *Saccharomyces boulardii* | HANSON CBS 5926 |
| *Saccharomyces boulardii* | CNCM I-3799 |

In preferred embodiments, one or more strains of *Lactobacillus helveticus* are selected from the following table.

| Species | Strain |
|---|---|
| *Lactobacillus helveticus* | Lafti L10 ND |
| *Lactobacillus helveticus* | Rosell-52 |
| *Lactobacillus helveticus* | GPS 4201 |
| *Lactobacillus helveticus* | GPS 4228 |
| *Lactobacillus helveticus* | HA 128 |
| *Lactobacillus helveticus* | HA-501 |
| *Lactobacillus helveticus* | L10 |
| *Lactobacillus helveticus* | LA 102 |
| *Lactobacillus helveticus* | LH 76 |

| Species | Strain |
|---|---|
| *Lactobacillus helveticus* | LH43 |
| *Lactobacillus helveticus* | LH76 |
| *Lactobacillus helveticus* | PXN 45 |
| *Lactobacillus helveticus* | R0052 |
| *Lactobacillus helveticus* | W74 |
| *Lactobacillus helveticus* | Candisis LA 401 |
| *Lactobacillus helveticus* | Candisis LA 402 |

In preferred embodiments, one or more strains of *Bifidobacterium bifidum* are selected from the following table.

| Species | Strain |
|---|---|
| *Bifidobacterium bifidum* | R0071 (Also known as CNCM I-3426) |
| *Bifidobacterium bifidum* | BB01 |
| *Bifidobacterium bifidum* | BB07 |
| *Bifidobacterium bifidum* | BB14 |
| *Bifidobacterium bifidum* | CUL-20 |
| *Bifidobacterium bifidum* | CUL-73 |
| *Bifidobacterium bifidum* | G9-1 |
| *Bifidobacterium bifidum* | ATCC 15696 |
| *Bifidobacterium bifidum* | PXN 23 |
| *Bifidobacterium bifidum* | W23 |

Form of Microbes

In preferred embodiments the microbes specified as part of the various aspects of the invention are provided in a viable or substantially viable form. Typically this may be in a freeze dried or otherwise preserved form in which metabolic activity is low but wherein a material proportion of the cells retain the ability to increase their metabolic activity and optionally multiply under appropriate conditions.

Level of Specified Microbial Organisms

The number of viable cells of each of the specified microbial species is conveniently expressed in terms of colony-forming units (CFUs). This may be assessed by any appropriate method. For example as outlined in Goldman, Emanuel; Green, Lorrence H Practical Handbook of Microbiology, Second Edition (Second ed.). USA: CRC Press, Taylor and Francis Group. p. 864. ISBN 978-0-8493-9365-5 (herein incorporated by reference).

According to certain embodiments of the invention the total amount of bacteria present in a composition according to the invention is about $20\times10^9$ CFU at the point of manufacture. In some embodiments, the total amount of *Lactobacillus paracasei* in a composition of the invention may be between about $1\times10^9$ and about $20\times10^9$ CFU, and optionally the total amount of *Bifidobacterium bifidum* may be between about $1\times10^9$ and about $19\times10^9$ CFU if present in the composition, and optionally the total amount of *Lactobacillus helveticus* may be between about $1\times10^9$ and about $19\times10^9$ CFU if present in the composition. In such embodiments, if the composition comprises two or more of *Lactobacillus paracasei, Bifidobacterium bifidum* and *Lactobacillus helveticus*, the combined total number of CFU of all bacterial species may not exceed $20\times10^9$ CFU. For example, the total amount of *Bifidobacterium bifidum* may be $4\times10^9$ CFU, the total amount of *Lactobacillus paracasei* may be $12\times10^9$ CFU, and the total amount of *Lactobacillus helveticus* may be $4\times10^9$ CFU, at the point of manufacture.

It is likely that in most compositions there will also be a certain level of non-viable cells and/or cell debris. However according to certain embodiments, viable microbial cells in total make up at least 5, 10, 20, 30, 40, 50, 60, or 70% of the total weight of the composition.

After the point of manufacture, the amount of bacteria present in the composition will decrease owing to die-off. A convenient way of expressing this is by determining the minimum amount of bacteria present at the best before date or the minimum amount of bacteria present at the date the composition is orally administered. According to certain embodiments the total amount of *Lactobacillus paracasei* and *Saccharomyces boulardii*, and optionally each of *Lactobacillus helveticus* and *Bifidobacterium bifidum*, in the composition at the point of oral administration and/or at the best before date of the composition is at least $2\times10^9$ CFUs, at least $5\times10^9$ CFUs, or as much as $10\times10^9$ CFUs, at the point of oral administration of the composition.

Zinc

In certain embodiments, zinc is present. Zinc is preferably present in the form of Zn2+ ions, preferably as zinc oxide (ZnO). The zinc oxide is preferably provided as a powdered solid. Alternative or additional sources of zinc include zinc citrate, zinc picolinate, zinc sulphate, chelated zinc (zinc bisglycinate), zinc gluconate, zinc-L-ascorbate, zinc chloride, zinc carbonate or inactive yeast zinc sulphate.

According to certain embodiments, zinc may be provided in a compound such as zinc oxide, which is present in an amount between 0.1 mg and 25 mg per dosage form. For example, between 1 mg and 20 mg per dosage form, preferably between 1.5 mg and 15 mg per dosage form, for example 1.5 mg, 2 mg, or 10 mg per dosage form. In some embodiments, zinc may be present in up to 25 mg per dosage form.

In some embodiments, a total of 10 mg of zinc is provided to a subject each day. A 10 mg dose of zinc per day is equivalent to 100% of the Nutrient Reference Value for an average adult in Europe. The total amount of zinc delivered to a subject may be in one or multiple doses. For example, a subject may receive multiple doses per day, with the total amount of zinc delivered to the subject not exceeding 25 mg per day, preferably not exceeding 10 mg per day. Alternatively, the subject may receive only one dose per day with a single dose not having a zinc content exceeding 25 mg, preferably not exceeding 10 mg, per day.

Other Ingredients

Compositions according to the invention may contain one or more further ingredients. Preferably these additional ingredients are generally recognised as safe or are approved for cosmetic, food and/or pharmaceutical use.

Exemplary compositions for oral administration may contain diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxypropyl cellulose (HPC), hydroxypropyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavours, colouring agents and stabilizers may also be added for ease of fabrication and use. For example, one or more antioxidant such as ascorbic acid, and/or one or more anticaking agents such as vegetable magnesium stearate, potato starch and ground rice hull (for example, the commercially available product Ribus), may be included as additional ingredients in compositions according to the invention. In certain preferred embodiments the compositions of the invention further comprise potato starch and ascorbic acid It has been found that, surprisingly, compositions of the invention can be effective when provided in a dosage form which lacks an enteric coating. It has been found that the preferred strains of compositions of the invention are naturally resistant to gastric acidity and that they are also stable during manufacture and storage. Further protection against stomach acid may be provided by providing the microorganisms of in compositions of the invention wherein they are provided in a matrix of potato starch and in the presence of ascorbic acid.

Dosage Forms

Compositions of the invention may optionally be provided in the form of single dosage forms. Suitable dosage forms include tablets, liquids, capsules, and sachets of powders, each containing a predetermined amount of the ingredients. Other suitable dosage forms include chewable tablets, gummies (for example chewable confectionery) and chewing gum.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release.

In certain embodiments the composition is provided as a dosage form which is a capsule. Any suitable capsule shell may be used and the ingredients of the dosage form may be provided as powder or granules inside the capsule shell.

If the compositions are not provided in a single dosage form, for example if they are provided as a powder for use as a food supplement or as a liquid to drink, they are preferably provided in a container with dosage instructions and may additionally be provided with a device (such as a spoon or scoop) for conveniently measuring the preferred dosage.

In preferred embodiments the dosage form lacks an enteric coating and comprises the specified bacteria and yeast species or preferred strains thereof in a matric of potato starch in the presence of ascorbic acid.

Cosmetic and Therapeutic Methods

The present invention provides a cosmetic benefit to the user. For example, it improves the appearance of skin. However in certain embodiments, certain aspects of the invention, may arguably be regarded as relating to therapeutic methods for preventing or treating a disease or disorder. It is acknowledged that in some jurisdictions, claims to methods of treating or preventing a disorder (for example claims to a method of preventing acne vulgaris) may be regarded as patentable subject matter whereas in other jurisdictions such methods may be regarded as excluded subject matter. In this regard the applicant reserves the right to amend the claims to comply with jurisdiction-specific subject matter requirements. For example, the applicant envisages limiting any method of the invention in accordance with any embodiment to cosmetic methods or to non-therapeutic methods, or to methods which are not methods of treating the human or animal body by therapy. Similarly, the applicant envisages claiming any embodiment of any aspect of the invention in "medical use" format. For example in "Swiss form" claim format, or in the statutory first or second medical use formats provided for in the European Patent Convention, the UK Patent Act 1977 and the law of other jurisdictions.

Cosmetic Method and Uses

Cosmetic methods and uses envisaged by the present invention include methods of improving the appearance of skin, especially of facial skin, for example by increasing the elasticity of the skin, increasing the hydration of the skin, changing the sebum secretion levels of the skin, reducing the roughness of the skin, reducing redness of the skin, increasing the smoothness of the skin, reducing trans-epidermal water loss and/or reducing the appearance of wrinkles and fine lines. The cosmetic methods and uses envisaged by the present invention may additionally or alternatively include methods of improving the appearance of skin by decreasing imperfections and problem areas associated with fatigue of the skin over time (i.e. an improvement in fatigability of the skin). Without wishing to be bound by theory, a decrease in fatigability of the skin may indicate an improvement of the cutaneous state.

A change of the sebum secretion levels includes altering the amount of sebum secreted by sebaceous glands of the skin to be within a normal range of values (about 100 to about 220 μg/cm$^2$ sebum secretion). For example, sebum secretion levels may be normalised by orally administering a composition of the invention to a subject which results in an increase in secretion of sebum in that subject. This may be particularly advantageous in those subjects that experience under-secretion of sebum. Herein, an under-secretion of serum is defined as a concentration equal to or less than 100 μg/cm$^2$ of sebum. A person having an under-secretion of sebum may experience dry skin. An increase in sebum concentration may result in an improvement in the appearance of the skin, such as a reduction in dryness, redness or flaking or cracking of the skin. Additionally, or alternatively, sebum secretion levels may be normalised by orally administering a composition of the invention to a subject which results in a decrease in secretion of sebum. This may be particularly advantageous in those subjects that experience an over-secretion of sebum. Herein, an over-secretion of sebum is defined as a concentration equal to or greater than 220 μg/cm$^2$ of sebum. A person having an over-secretion of sebum may experience oily or greasy skin. A reduction in sebum concentration may result in an improvement in the appearance of the skin, such as a reduction in an oily or greasy appearance. In some embodiments the sebum secretion concentration of a subject is normalised by administration of a composition according to the invention, so that the sebum secretion concentration of the subject is altered so that it falls between the normal range of between 100-220 μg/cm$^2$ of sebum. Thus, in the case of a person having an average sebum secretion concentration below 100 μg/cm$^2$ before treatment, administration of a composition of the invention to the subject results in an increase in average sebum concentration to between 100-220 μg/cm$^2$ of sebum. In the case of a person having an average sebum secretion concentration above 220 μg/cm$^2$ before treatment, administration of a composition of the invention to the subject results in a decrease in average sebum concentration to between 100-220 μg/cm$^2$ of sebum.

The change in appearance of the skin may be exhibited in any area of the body, for example the face, neck and/or back. The appearance of the skin may be improved within regions of the body area. For example, an improvement in the appearance of the skin of the face may occur in the nose, forehead, cheeks, chin or upper lip region of the face.

The present invention also envisages use of compositions of the present invention in any of the cosmetic uses disclosed herein.

Medical Methods

Therapeutic methods and uses envisaged by the present invention include the use of a composition of the invention as a medicament. For example, a composition of the invention may be used to treat a skin disease, such as an inflammatory disease of the skin. In certain embodiments, a composition of the invention may be used to treat acne vulgaris.

In some embodiments the composition of the invention may be used to treat immune diseases of the skin, for example atopic dermatitis (eczema) and/or psoriasis.

According to an aspect of the invention, it is envisaged that the composition of the invention may alter the microbiome of the skin of a subject, particularly the skin of the face. For example, oral administration of a composition of the invention may result in a normalisation of the concentration of the bacteria *Cutibacterium* acnes found on the skin. The normalisation of concentration of *Cutibacterium* acnes may involve an increase in the concentration of *Cutibacterium* acnes, for example if the subject to which the composition has been administered had a below average concentration of *Cutibacterium* acnes before treatment. Alternatively, the normalisation of concentration of *Cutibacterium* acnes may involve a decrease of the bacteria *Cutibacterium* acnes found on the skin. For example, if the subject to which the composition is administered had an above average concentration of *Cutibacterium* acnes before treatment. Herein, the concentration of *Cutibacterium* acnes may be determined by carrying out any suitable assay for example RT-ribotyping and explained in Tomida S, Nguyen L, Chiu B, Liu J, Sodergren E, Weinstock GM, Li H. 2013. Pan-genome and comparative genome analyses of *Propionibacterium* acnes reveal its genomic diversity in the healthy and diseased human skin microbiome. mBio 4(3):e00003-13. doi:10.1128/mBio.00003-13.

Preventative methods and uses envisaged by the present invention include the use of a composition of the invention as a medicament. For example, a composition of the invention may be used to prevent a skin disease, such as an inflammatory disease of the skin. In certain embodiments, a composition of the invention may be used to treat acne vulgaris, atopic dermatitis, psoriasis and/or rosacea.

In some embodiments the composition of the invention may be used to prevent immune diseases of the skin, for example atopic dermatitis (eczema) and/or psoriasis. In such cases, a subject or patient may be administered a composition of the invention before presenting symptoms of the disease. In some embodiments, a subject or patient may be administered a composition of the invention before prevention symptoms of a disease, but if they have previously experienced symptoms of such as disease in the past.

In some embodiments of the invention, it is envisaged that a composition of the invention may reduce sebum production by sebaceous glands of the skin, in particular of the skin of the face. *Cutibacterium* acnes feeds on the fatty acids found in sebum. Therefore, without wishing to be bound by theory, a reduction in the amount of sebum produced may also result in a reduction in *Cutibacterium* acnes found on the skin. This is turn may reduce the symptoms of acne vulgaris. Additionally, a reduction in the amount of sebum produced by the sebaceous glands may result in the treatment of acnes vulgaris.

In some embodiments, the symptoms of a skin disease may be reduced or eliminated by oral administration of a composition according to the invention. For example, symptoms associated with acne vulgaris, such as skin redness, dryness, comedones and pimples, cysts and nodules result in scarring may be reduced or alleviated. Without wishing to be bound by theory, a reduction in the sebum concentration on the skin, particularly of the skin of the face, may result in a reduction of the symptoms of acne vulgaris because sebum causes ductal blockage and inflammation of the skin.

Subjects to be Treated

In some embodiments of the invention the subjects to be treated are male. In some embodiments of the invention the subjects are female. In some embodiments, the subject is aged between 10 and 75 years, for example between 12 and 35 years. In preferred embodiments, the subjects are adolescent (between 10 and 19 years). In preferred embodiments, the subject is between 18 and 35 years old, for example between 20 and 30 years old. It will be understood that adolescents and subjects between 18 and 30 years of age are particularly prone to inflammatory skin diseases such as acne vulgaris, as well as "problem skin" such as oily skin, dry skin, or blemished or reddened skin.

In some embodiments, the subjects are individuals suffering from an inflammatory skin disease. In some embodiments, the inflammatory skin disease is acne vulgaris, atopic dermatitis, psoriasis and rosacea. In some embodiments, the subject is suffering from a skin disease caused by an immune response, for example psoriasis or atopic dermatitis.

In some embodiments, the subjects are individuals prone to, but not currently suffering from a skin disease, for example individuals who previously suffered from a skin disease. The skin disease may for example be acnes vulgaris, atopic dermatitis or psoriasis.

In some embodiments, subjects may be individuals with excessively dry or excessively greasy skin or regions thereof.

In some embodiments, subjects may be individuals with a microbiome imbalance of the skin, caused for example, by medical treatment such as antibiotics or steroid hormones, or by dietary issues, stress or other illnesses.

Skin to be Treated

It is envisaged by the present invention that the skin to be treated includes the back, chest (especially décolletage), neck, face (for example chin, nose, forehead, cheeks, jawline or upper lip region), and areas irritated by clothing (such as waistband, collar, bra strap) or accessories (such as watch straps, glasses, and face masks). Additionally or alternatively, it is envisaged by the present invention that the skin to be treated includes the torso, arms, legs, hands or scalp.

Dosage Regimens

According to some embodiments a composition according of the invention may be orally administered once a day or multiple times a day, for example twice a day, three times a day or more than three times a day. In some embodiments the composition is administered at the same time each day.

According to some embodiments the composition is orally administered on a daily basis as described above, and is administered continually for multiple, consecutive days, for example each day for a week, each day for a month or each day for multiple months, such as for three months. In some embodiments the composition is administered each day indefinitely. In some embodiments the composition is administered every day until symptoms no longer persist or a disease has been treated. In some embodiments the composition is orally administered on alternative days, for example every other day, or one day per week.

The dosage may be delivered as one or more capsules. One capsule or more may be taken a day, for example two or more capsules per day, three or more capsules per day, five or more capsules per day or as many as ten or more capsules per day.

In some embodiments, the composition of the invention is administered to a subject in combination with a further treatment. The further treatment may be the use of one or more of a cleanser, exfoliator or moisturiser. Alternatively or additionally the further treatment may be a medical light emitting device.

In some embodiments, the composition of the invention is administered to a subject in combination with one or more of the following: prebiotics, postbiotics, vitamins, minerals, fats and phytonutrients, and botanicals.

EXAMPLES

Equipment

The skin function was measured using non-invasive measurements and the following properties were assessed according to methods known in the art: skin elasticity, hydration (water content), transepidermal water loss, sebum levels, roughness, redness, and smoothness of the skin surface. A Courage+Khazaka Dual 580 Multi Probe Adapter System (MPA) was used for skin measurements, fitted with the following probes. A Cutometer was used to measure skin elasticity. A Corneometer was used to measure skin hydration. A Tewameter was used to measure transepidermal water loss. A Sebumeter (Model SM 815) was used to determine sebum levels. A Visioscan VC 98 and Canfield's Visia skin analysis imaging system was used to study the skin surface and determine properties such as skin smoothness, skin roughness, scaliness and wrinkles and to measure spots, wrinkles, texture, pores, UV spots, brown spots, red areas and porphyrins. All devices were manufactured and maintained according to the cosmetic industry standards for non-invasive technologies for assessing the various parameters of skin.

A Cutometer uses a suction method to determine the elasticity and firmness of the skin. A negative pressure is applied to the skin which causes it to mechanically deform by drawing the skin into an aperture within the device. After a period of time, the skin is released from the device. The penetration depth of the skin within the device is measured by an optical measuring system comprising a light source and a light receptor. Light is projected onto the skin and the light intensity returned to the light receptor varies depending on the penetration depth of the skin. The penetration depth in mm/time is measured in real time and the resistance of the skin to negative pressure (firmness) and its ability to return to its original position (elasticity) are recorded.

A Corneometer was used to measure the hydration of the skin surface (about 10-20 μm depth of the stratum corneum). This probe allows quick measurements (about 1 s) to be taken, and also allows continuous measurements to be taken over a prolonged period of time. The probe works by measuring the capacitance of the uppermost layer of the skin, the stratum corneum. With increasing hydration, the dielectric properties of the skin change. Water has a high dielectric constant compared to most other substances. The Corneometer measures the change in the dielectric constant due to skin surface hydration changing the capacitance of a precision capacitor and is sensitive to very small changes in hydration level of the skin.

A Tewameter is used to assess transepidermal water loss which is a parameter for evaluating the water barrier function of the skin. If the barrier function of the skin is damaged, this will result in an increase in water loss. The Tewameter probe is a hollow cylinder containing sensors to measure relative humidity and temperature. The probe measures the density gradient of the water evaporation from the skin which is proportional to the transepidermal water loss. Transepidermal water loss is measured in $g/m^2/h$ and can be used to measure skin functionality, in particular barrier function.

A Sebumeter is used to determine the sebum level of the skin surface. The sebumeter contains a tape which reacts with sebum to become transparent. The tape is placed in contact with the skin to allow the tape to react to sebum and then the transparency of the tape is measured by inserting the tape into an aperture in the device and measuring the transparency by a photocell.

Full face photos were taken with a Visia machine (Canfield) with Visioscan VC 98 imager both before and after the subject was administered a composition according to the invention. The Visia machine (Canfield) uses cross-polarized and UV lighting to record and measure surface and subsurface skin conditions. UV photography provides the most complete data set available for sun damage assessment and analysis, including UV fluorescence imaging to reveal porphyrins, spots, wrinkles, texture, pores, brown spots, red areas and UV spots. The images were assessed for visual changes in appearance of the skin, for example a reduction in skin redness, dryness, dullness, or oiliness, or a generally more healthy appearance of the skin following administration of the inventive composition.

Biomass on the skin of the face was collected using a standard swabbing method. The forehead, nose and chin of each subject was swabbed and analysed separately. The skin of the face was swabbed using a collection kit comprising Geneflow Swab Collection & DNA preservation kit & Norgren wetting tube. The microbiome of the skin may be analysed by 16s rRNA analysis. Alternatively, or additionally, the microbiome of the skin may be analysed by UV imaging in which porphyrins produced by Cutibacterium acnes fluoresce under UV irradiation (near 400 nm). UV facial images were taken before and after the subject had been orally administered a composition according to the invention each day for 4 weeks. A reduction in the amount of fluorescence associated with porphyrins was indicative of a reduction in *Cutibacterium* acnes present on the skin.

Bacterial and yeast strains were purchased from Lallemand (Mirabel, Canada) and, incorporated into the final formula.

Trial

Subject Selection

Healthy female adult volunteers were selected for the trial. Subjects selected for the trial fell into each of the Fitzpatrick skin classification I, II, III, IV, and V and were within the age range of 25-35 years. None of the subjects had known skin problems.

The following subjects were excluded from the study. Those below the age of 18 years; pregnant or breastfeeding women; subjects taking antibiotics 2 months prior and up to the study; subjects using topical antibacterial creams; subjects taking prescription medications, including warfarin; subjects with an impaired immune system due to immunosuppressive diseases such as AIDS and HIV, or use of immunosuppressive medications; subjects with a history of active uncontrolled gastrointestinal disorders or diseases including: inflammatory bowel disease (IBD) including ulcerative colitis (mild-moderate-severe), Crohn's disease (mild-moderate-severe), or indeterminate colitis, subjects with irritable bowel syndrome (IBS) (moderate-severe); subjects unable to communicate or cooperate with the investigators due to language problems or impaired cerebral functions.

The duration of the trial was 4 weeks, with subjects assessed before and after commencing the trial in order to determine changes to the skin of the face of the subject. The number of individuals used in the study was 17.

Trial Regime

Two weeks before the commencement date of the trial (the date on which the subject was first administered a composition according to the present invention), subjects underwent a two week "washout period" in which they stopped taking all food supplements and probiotic supplements. 48 hours prior to the commencement date of the trial, subjects were required to refrain from using any antibacterial products or antiseptic products on the face. The subjects were also required to avoid swimming in chlorinated water, and using a hot tub or sauna. The evening prior to the commencement date of the trial, the subjects were required to wash their face with soap cleanser and makeup was removed. The subjects' face must not have been washed any later than 7 pm on the evening before the commencement date of the trial.

On the morning of the commencement date, or first date, of the trial, subjects were required to avoid scrubbing or thoroughly washing their face. It was permitted to splash water only on the face and the skin could be gently patted dry. Each subject's skin was then assessed. The skin of the face was swabbed using a collection kit comprising Geneflow Swab Collection & DNA preservation kit & Norgren wetting tube. Different swabs were used for the forehead, nose and chin area of the face. Measurements were also taken of the forehead, nose and chin areas of the face using a set of probes as described above. A full face photo was also taken with the Visia equipment.

After the assessment, the participants were each given a 4 week supply of composition A, the composition of which is described in Table 1. Each subject received a single daily dose of Composition A of 1 capsule with the first dose taken on the day of the first assessment (the commencement date of the trial) and the last capsule taken on the day of the second assessment (or end date of the trial). In total, each subject was orally administered 1 capsule per day for 4 weeks. The second assessment was also the final assessment of the trial. During the 4 week period of the trial, subjects were required to refrain from using any antibacterial products on their face. The subjects were permitted to apply topical cosmetics such as creams and makeup. If a subject was prescribed antibiotics by a doctor during the 4 week trial, they were required to make this known immediately.

TABLE 1

| Composition A per capsule at manufacture | |
|---|---|
| Component | Amount* |
| *Lactobacillus paracasei* (Lafti L26 AF) | >12 × $10^9$ CFU |
| *Bifidobacterium bifidum* (Rosell-71 (R0071)) | >4 × $10^9$ CFU |
| *Lactobacillus helveticus* (Lafti L10 ND) | >4 × $10^9$ CFU |
| *Saccharomyces boulardii* (*Saccharomyces cerevisiae boulardii* CNCM -I-1079) | >2.5 × $10^9$ CFU |
| Zinc oxide | 2.6 mg (20% Nutrients reference value) |

*CFU is colony forming units

The total amount of bacteria present in a composition according to the invention was about $20\times10^9$ CFU at the point of manufacture. The total amount of *Bifidobacterium*

*bifidum* was about $4\times10^9$ CFU, the total amount of *Lactobacillus paracasei* was about $12\times10^9$ CFU, and the total amount of *Lactobacillus helveticus* was about $4\times10^9$ CFU at the point of manufacture. The total amount of bacteria and yeast present in the capsule at the best before use date is at least $5\times10^9$ CFUs.

The composition A was formed into a capsule further comprising a vegetable capsule shell (hydroxypropyl methylcellulose), antioxidant (ascorbic acid), anti-caking agent: vegetable magnesium stearate, and potato starch.

*Lactobacillus paracasei, Lactobacillus helveticus* and *Saccharomyces boulardii* are all naturally present in fermented foods. *Bifidobacterium bifidum* is naturally present in the human digestive tract and is one of the first bacteria to colonise the gut when a human is born. Zinc oxide is an important mineral involved in the maintenance of hair, nails and skin and is found in foods such as cashew nuts, spinach and asparagus.

The skin of each subject was assessed at the beginning of the four week trial, and again during a second assessment at the end of the four week trial period. At the second assessment, the same assessment procedure was used as that described above for the first assessment. Again, 48 hours before the second assessment, subjects were required to refrain from using antibacterial products or antiseptic products on the face. Subjects were also asked to refrain from swimming in chlorinated water, using a hot tub or a sauna. The evening prior to the assessment, subjects were permitted to wash the face with soap cleanser and to remove all makeup from the face. The face was washed no later than 7 pm the evening before the second assessment. On the morning of the second assessment, the face was only permitted to be washed with water and gently patted dry. Thorough washing or scrubbing of the face was not permitted.

The abundance of porphyrin on the face of each subject was assessed at the first assessment (the commencement date of the trial) and at the second assessment (the last date of the trial). The results are shown in Table 2.

TABLE 2

Porphyrin concentration at the first and second assessment of each subject.

| Subject | Baseline (first assessment) | Week 4 (second assessment) | Difference |
|---|---|---|---|
| 1 | 4932 | 3935 | −997 |
| 2 | 4263 | 3016 | −1247 |
| 3 | 2981 | 2928 | −53 |
| 4 | 2113 | 1985 | −128 |
| 5 | 1884 | 1377 | −507 |
| 6 | 1164 | 835 | −329 |
| 7 | 1028 | 883 | −145 |
| 8 | 929 | 797 | −132 |
| 9 | 783 | 586 | −197 |
| 10 | 1422 | 1619 | 197 |
| 11 | 1427 | 2171 | 744 |
| 12 | 380 | 599 | 219 |
| 13 | 2129 | 2815 | 686 |
| 14 | 1602 | 2218 | 616 |
| 15 | 810 | 1106 | 296 |
| 16 | N/A | N/A | N/A |
| 17 | N/A | N/A | N/A |
| Average | 1856 | 1791 | −65 |

As shown in Table 2, 9 out of the 17 subjects (subject 16 & 17 excluded) assessed experienced a reduction in porphyrins on the skin of the face following the 4 week trial, during which they received a daily dose of composition A. Interestingly, in both subjects with particularly high porphyrin concentrations in excess of 4000 at the first assessment (subject 1 and 2) a reduction in porphyrin concentrations was observed at the second assessment. All but one of the subjects with porphyrin concentrations in excess of 2000 experienced a reduction in porphyrin concentration at the second assessment.

A change in porphyrin levels on the skin is indicative of a change in *Cutibacterium* acnes which produces the porphyrins, and therefore suggests the microbiome of the subject has been altered by oral administration of compound A. Composition A may be an effective treatment for acnes vulgaris which is associated with an excess of *Cutibacterium* acnes on the skin.

FIGS. 1-4 show images taken of the skin of subject 2 with a Visioscan VC 98 imager at the first and second assessment. FIG. 1 shows the forehead region of subject 2 at the first assessment. The fluorescence of porphyrins is exhibited as orange dot like marks on the skin (shown as white dots in the black and white FIG. 1). The lower image of FIG. 1 shows an expanded view of the central portion of the forehead within the rectangular box shown in the upper image. As can be seen from FIG. 1, subject 2 had a high concentration of porphyrins on the skin of the forehead on the commencement date of the trial.

Figure 2:
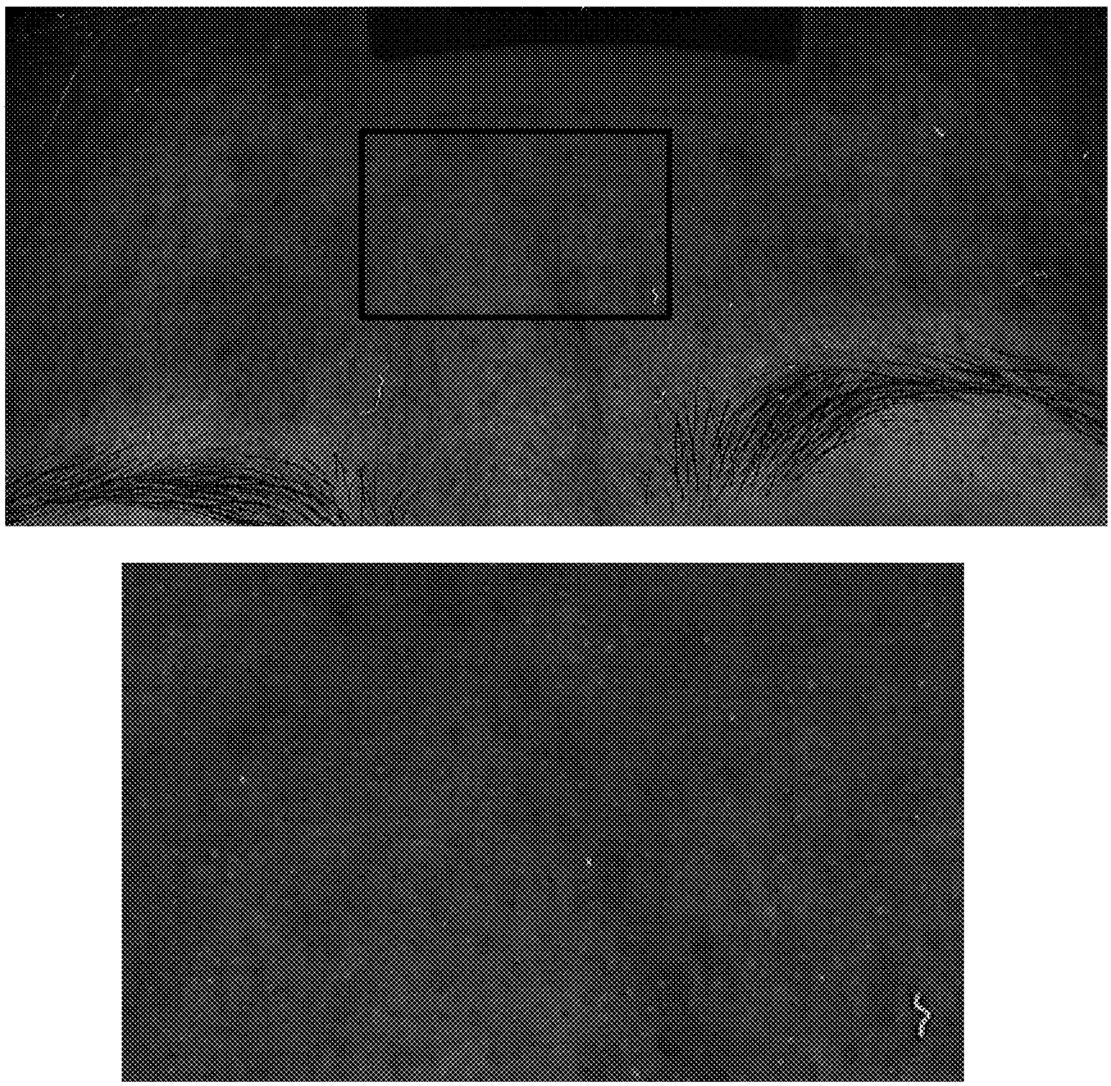
FIG. 2 shows an image taken of the forehead of subject 2 with UV (near 400 nm) facial imaging equipment after composition A was administered once per day for 4 weeks. The lower image is an expanded image of the section of the forehead highlighted in a box in the upper image. A reduction in the white regions on the skin (corresponding to orange regions in the colour image) is indicative of a reduction in porphyrin on the skin.

FIG. 2 shows the forehead region of subject 2 at the second assessment. The lower image of FIG. 2 shows an expanded view of the central portion of the forehead within the rectangular box shown in the upper image. As can be seen from FIG. 2 when compared to FIG. 1, subject 2 had a reduction in concentration of porphyrins on the skin of the forehead on the final date of the trial compared to the commencement date.

Figure 3:
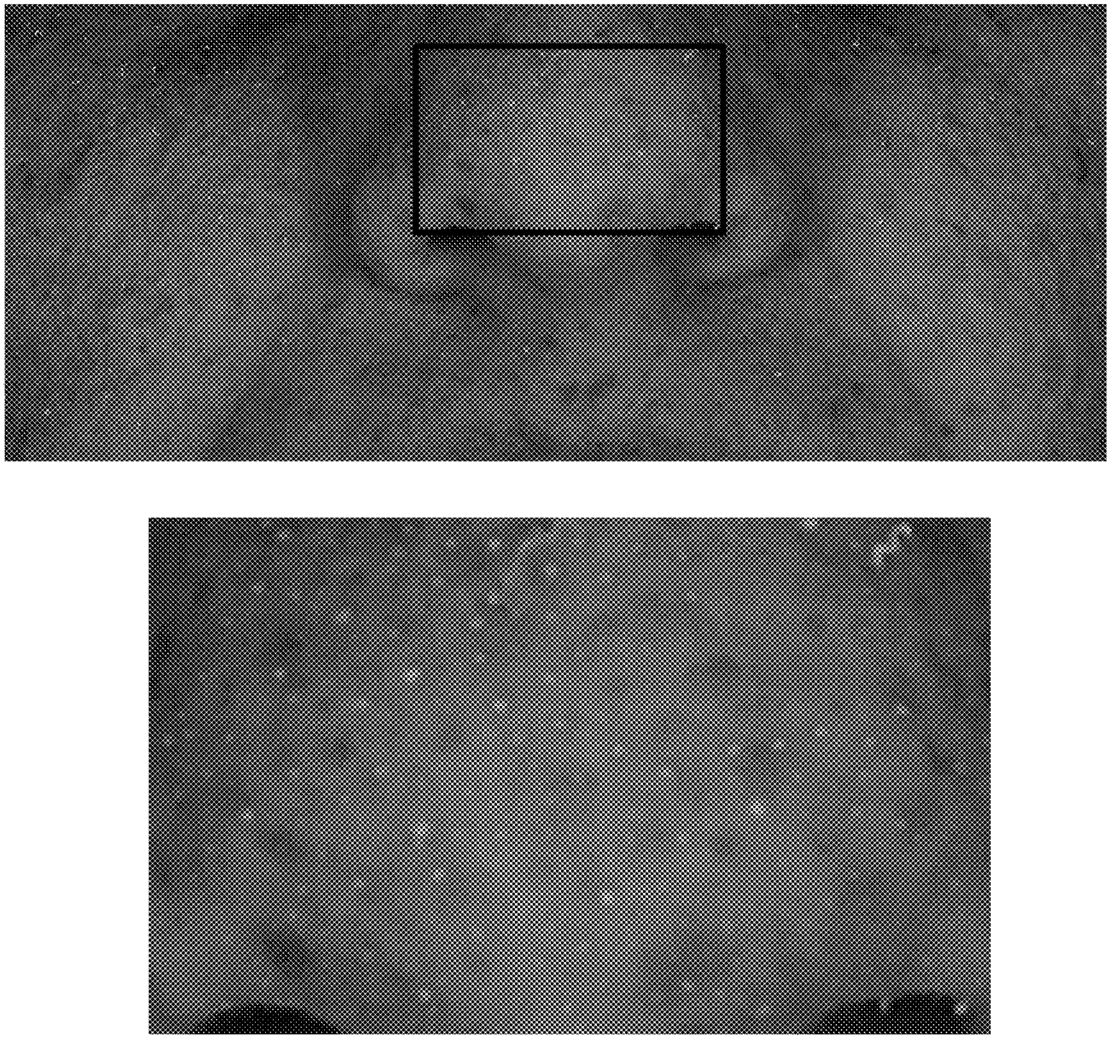
FIG. 3 shows an image taken of the nose, upper lip and cheek area of subject 2 with UV (near 400 nm) facial imaging equipment before composition A was administered. The lower image is an expanded image of the section of the forehead highlighted in a box in the upper image. The white regions on the skin (corresponding to orange regions in the colour image) are caused by porphyrins that fluoresce under UV light.

FIG. 3 shows the nose, cheek and upper lip region of subject 2 at the first assessment. Again, the fluorescence of porphyrins is exhibited as white dot like marks on the skin. The lower image of FIG. 3 shows an expanded view of the central portion of the nose within the rectangular box shown in the upper image. As can be seen from FIG. 3, subject 2 had a high concentration of porphyrins on the skin of the nose in particular on the commencement date of the trial.

Figure 4:
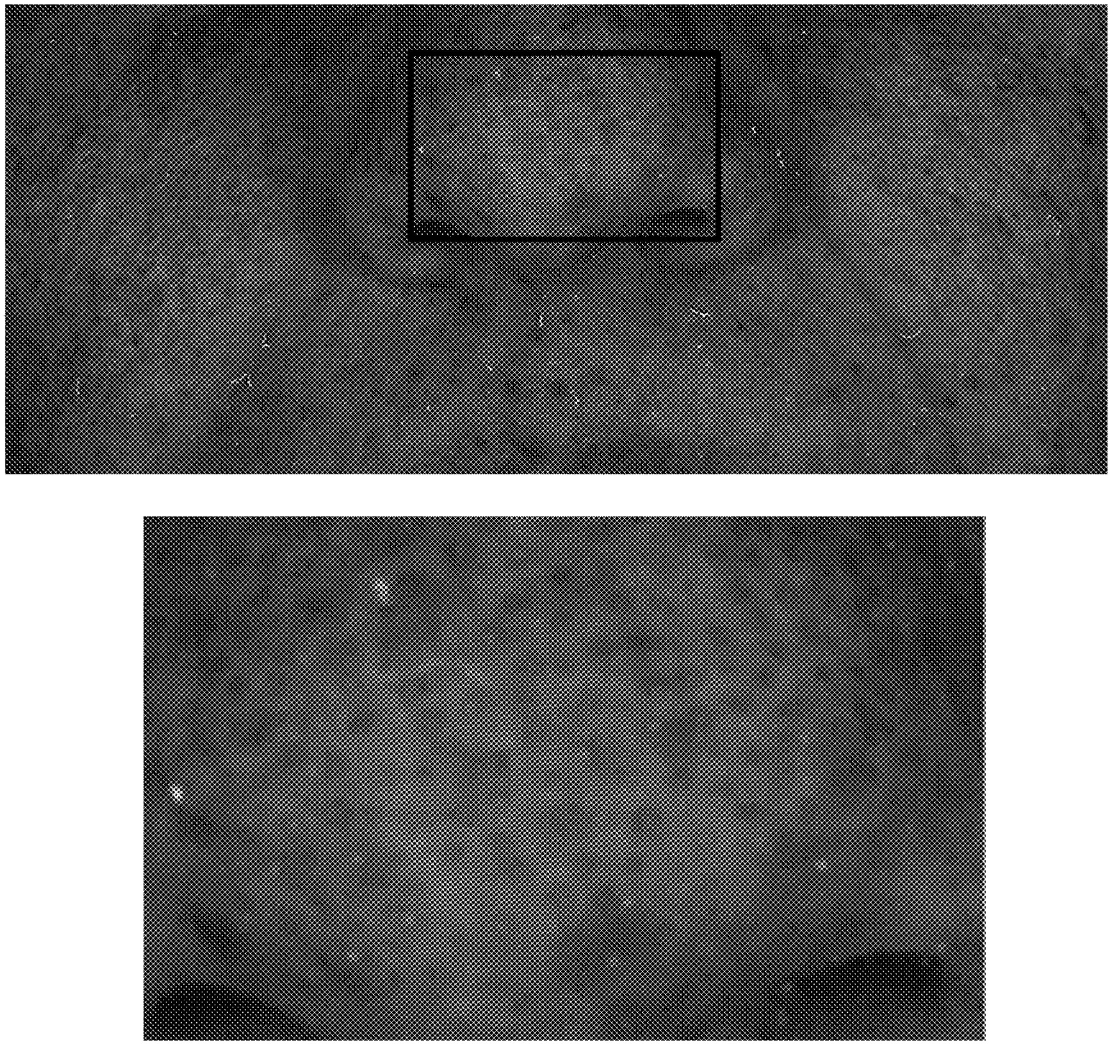
FIG. 4 shows an image taken of the nose, upper lip and cheek area of subject 2 with UV (near 400 nm) facial imaging equipment after composition A was administered once per day for 4 weeks. The lower image is an expanded image of the section of the forehead highlighted in a box in the upper image. A reduction in the white regions on the skin (corresponding to orange regions in the colour image) is indicative of a reduction in porphyrin on the skin.

FIG. 4 shows the nose, cheek and upper lip region of subject 2 at the second assessment. The lower image of FIG. 4 shows an expanded view of the central portion of the nose within the rectangular box shown in the upper image. As can be seen from FIG. 4 when compared to FIG. 3, subject 2 had a reduction in concentration of porphyrins on the skin of the nose in particular on the final date of the trial compared to the commencement date.

The sebum level of the skin of each subject was also determined at the first and second assessment, as shown in Table 3. The sebum level of the forehead, nose and chin region of each subject was assessed. Sebum is secreted by sebaceous glands of the skin. A low concentration of sebum of the skin may be associated with dry, flaky or dull looking skin. However, a high concentration of sebum of the skin may be associated with oily or greasy looking skin. It is therefore desirable to obtain a concentration of sebum within normal parameters in order to improve the appearance of the skin. Sebum may be associated with the inflammatory skin condition acne vulgaris. Therefore a reduction in sebum production in those subjects experiencing over-secretion may reduce the appearance of comedones and pimples produced as a symptom of this condition. Advantageously, a reduction in sebum secretion in subjects experiencing over-secretion may treat acne vulgaris. Therefore, a normalisation in sebum production to concentrations within normal levels (average sebum concentration of between 100 and 220 μg/cm$^2$) may have both cosmetic and therapeutic benefits.

As shown in Table 3, on average the subjects experienced a reduction in sebum secretion on the skin of the forehead, nose and chin. Interestingly, subject 9 had extremely dry skin at the first assessment as indicated by low sebum levels. However, at the end of the 4 week trial, the sebum levels had increased as shown at the second assessment. This indicates that composition A may have a normalising effect on the concentration of sebum produced on the skin, bringing sebum production with normal ranges. For example, those subjects who experienced over-secretion of sebum may have experiences a reduction in sebum production following administration of composition A. Those subjects who experienced an under-secretion of sebum, may have experienced an increase in sebum production following administration of composition A.

Skin swabs of the forehead comprising of 20 total samples from 10 subjects which were taken to characterize the skin microbiome both before and after treatment ('before' and 'after' samples). Bacterial samples were collected from the forehead area using a Geneflow Swab Collection & DNA preservation kit & Norgren wetting tube. To assess the microbiome of the subjects, and how this changed before and after treatment, each sample was submitted for sequencing of the V1V3 region of the 16S rRNA gene using amplicon sequencing. Once generated, sequences were analysed using a modification of a standard pipeline for 16S amplicon analysis. This was done to statistically test whether any microbiome metrics were different between before and after samples submitted in this project. Specifically, we examined within-sample diversity differences (i.e. Alpha Diversity), between-sample diversity differences (i.e. Beta Diversity), and differential abundance of taxa between time points.

TABLE 3

The sebum concentration levels of the forehead, nose and chin of each subject as the first and second assessment.

| | Baseline (first assessment) | | | Week 4 (second assessment) | | | Difference | | | Percentage difference | | |
|---|---|---|---|---|---|---|---|---|---|---|---|---|
| Subject | Forehead | Nose | Chin | Forehead | Nose | Chin | Forehead | Nose | Chin | Forehead | Nose | Chin |
| 1 | 75 | 50 | 109 | 100 | 64 | 123 | 25 | 14 | 14 | 33 | 28 | 13 |
| 2 | 180 | 199 | 128 | 123 | 103 | 156 | −57 | −96 | 28 | −32 | −48 | 22 |
| 3 | N/A | N/A | N/A | N/A | N/A | N/A | N/A | N/A | N/A | N/A | N/A | N/A |
| 4 | 168 | 149 | 149 | 147 | 38 | 131 | −21 | −111 | −18 | −13 | −75 | −12 |
| 5 | 98 | 135 | 100 | 86 | 202 | 133 | −12 | 67 | 33 | −12 | 50 | 33 |
| 6 | 53 | 83 | 178 | 58 | 7 | 103 | 5 | −76 | −75 | 9 | −92 | −42 |
| 7 | N/A | N/A | N/A | N/A | N/A | N/A | N/A | N/A | N/A | N/A | N/A | N/A |
| 8 | 221 | 110 | 176 | 195 | 98 | 159 | −26 | −12 | −17 | −12 | −11 | −10 |
| 9 | 9 | 19 | 3 | 34 | 37 | 62 | 25 | 28 | 59 | 278 | 95 | 1967 |
| 10 | 97 | 67 | 61 | 78 | 33 | 51 | −19 | −34 | −10 | −20 | −51 | −16 |
| 11 | 147 | 70 | 79 | 88 | 74 | 63 | −59 5 | 4 | −16 | −40 | 5.7 | −20 |
| 12 | 126 | 185 | 154 | 98 | 42 | 38 | −28 | −143 | −116 | −22 | −77 | −75 5 |
| 13 | 129 | 102 | 53 | 63 | 37 | 92 | −66 | −65 | 39 | −51 | −64 | 74 |
| 14 | N/A | N/A | N/A | N/A | N/A | N/A | N/A | N/A | N/A | N/A | N/A | N/A |
| 15 | 56 | 105 | 159 | 131 | 66 | 24 | 75 | −39 | −135 | 134 | −37 | −85 |
| 16 | 237 | 166 | 154 | 234 | 93 | 128 | −3 | −73 | −26 | −1 | −44 | −17 |
| 17 | N/A | N/A | N/A | N/A | N/A | N/A | N/A | N/A | N/A | N/A | N/A | N/A |

Further Trial

A second trial was conducted to further investigate the effects of Composition A on subjects. The trial was carried out in the same manner as the first trial, except that the subjects took Composition A over a period of 8 weeks, rather than 4 weeks, and skin measurements were performed at 3 points, at the beginning of the study (baseline), midpoint (4 weeks) and at the end of the study (8 weeks). 14 subjects (1 male, 13 female), ages 19 to 40 years (mean age: 28 years), Fitzpatrick Skin Type 1 to VI, and from any ethnic group, participated in the 8-week study. Participants were instructed to take one capsule of Composition A per day with a meal, for an 8 week period.

16s rRNA (v1/v3 Region) Sequencing

Use of broad range 16S rRNA gene PCR as a tool for identification of bacteria is possible because the 16S rRNA gene is present in all bacteria. The 16S rRNA gene consists of highly conserved nucleotide sequences, interspersed with variable regions that are genus- or species-specific. PCR primers targeting the conserved regions of rRNA amplify variable sequences of the rRNA gene. Bacteria can be identified by nucleotide sequence analysis of the PCR product followed by comparison of this sequence with known sequences stored in a database (Jenkins, C., et al. (2012). Detection and identification of bacteria in clinical samples by 16S rRNA gene sequencing: comparison of two different approaches in clinical practice. Journal of Medical Microbiology, 61, 483-488).

Overall, no significant difference in Alpha and Beta diversity between time points was observed. There were no significant difference in abundance of taxons once p-values were corrected for multiple hypothesis testing. However, the uncorrected p-values from the differential taxa testing showed that three ASVs from two bacterial genera (*Lawsonella* and *Cutibacterium*) were significantly lower (uncorrected $p<0.05$) in the after samples when compared to the before samples.

Results and observations from Measure Yourself Medical Outcome Profile (MYMOP)

Participants completed a MYMOP (Measure Yourself Medical Outcome Profile) form at baseline, 4 weeks and at 8 weeks. MYMOP is a validated method to detect changes when symptoms in people improve or remain unchanged. This questionnaire allows people to nominate symptoms that are concerning them most and to subjectively assess the change of these symptoms over a period of time following a therapeutic intervention.

86% of participants reported an improvement in their skin problem symptoms. 93% of participants reported a change at 4 weeks. The improvement in skin problem symptoms within 4 weeks unexpected, with a longer period of treatment predicted to be needed to see a beneficial effect on the skin. In a comparison between base line and symptoms at week 8, 33% of participants reported an improvement in skin redness, 41% reported a reduction in frequency of breakouts, 35% reported a quicker healing time, and 38% reported increased confidence and wellbeing levels.

In a second self-assessment questionnaire, 64% of participants reported that their skin was less oily than usual.

Skin Measurements

At the end of the study, an improvement in the appearance of the skin of the participants was observed. For example, on average, the forehead area of the skin of the subjects reduced sebum production by 42% compared to the beginning of the study, the nose area of the skin reduced sebum production by 30% on average, and the chin area reduced sebum production by 28% on average, as measured by a Sebumeter 815.

The elasticity of the skin of the eye area increased by an average of 9% by the end of the 8-week trial, as measured by a Cutometer. The elasticity of the skin of the cheek increased by an average of 1%. A reduction in wrinkle depth was also observed, as measured by a Visioscan. On average, wrinkle depth decreased by 9% in the eye area and decreased by 6% in the cheek area. The skin also appeared smoother after the eight-week trial, as measured by a Visioscan. An average improvement in skin smoothness of 3% was observed in the eye area, and an improvement of 2% was observed in the cheek area. No improvement in skin hydration was observed after the 8-week trial, as measured by a Corneometer. An improvement in Transepidermal Water Loss (TEWL) was observed, as measured by a Tewameter. A decrease in TEWL of 12% on average was observed in the eye area and a decrease in TEWL of 1% on average was observed in the cheek area.

An improvement in the appearance of the skin was observed in participants, for example as measured with a Cranfield's Visia facial imager. For example, a reduction in skin redness was observed over the course of the treatment. 33% of participants also reported an improvement in redness. 71% of participants reported a reduction in spots. 42% of participants showed a reduction in pore size.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A composition formulated for oral delivery comprising freeze-dried *Lactobacillus paracasei* and *Saccharomyces boulardii*, wherein the *Lactobacillus paracasei* comprises the strain LAFTI® L26; and at least one of freeze-dried *Lactobacillus helveticus* and *Bifidobacterium bifidum*, wherein the composition is further formulated to provide a protective matrix to enhance intestinal colonization and improve shelf-life.

2. The composition according to claim 1, wherein the *Saccharomyces boulardii* comprises the strain *Saccharomyces cerevisiae* var. *boulardii* CNCM-I- 1079.

3. The composition according to claim 1, wherein the composition at the point of manufacture comprises between $1\times10^9$ and $20\times10^9$ colony forming units (CFUs) of *Lactobacillus paracasei* and between $1\times10^9$ and $4\times10^9$ CFU of *Saccharomyces boulardii.*

4. The composition according to claim 1, wherein the composition comprises at the point of manufacture between $1\times10^9$ and $8\times10^9$ CFUs of *Lactobacillus helveticus*, or wherein the composition comprises at the point of manufacture between $1\times10^9$ and $8\times10^9$ CFUs of *Bifidobacterium bifidum.*

5. The composition according to claim 1, further comprising zinc.

6. The composition of claim 3, wherein the composition comprises at least $12\times10^9$ CFUs of *Lactobacillus paracasei* and at least $2.5\times10^9$ CFUs of *Saccharomyces boulardii.*

7. The composition according to claim 1, wherein the composition is formulated to treat an inflammatory disease of the skin selected from the group consisting of acne vulgaris, atopic dermatitis, psoriasis and rosacea.

8. The composition according to claim 1, wherein the composition is in the form of a tablet, powder, capsule, drink or food.

9. The composition of claim 1, further comprising a prebiotic, postbiotic, vitamin, mineral, fat, phytonutrient, botanical, or combinations thereof.

10. The composition of claim 1, further comprising an antioxidant, an anticaking agent, or combinations thereof.

11. The composition of claim 10, wherein the antioxidant is ascorbic acid and the anticaking agent is potato starch, and wherein the composition is provided in a matrix to resist gastric acidity and provide stability during manufacture and storage.

* * * * *